Figure 1:
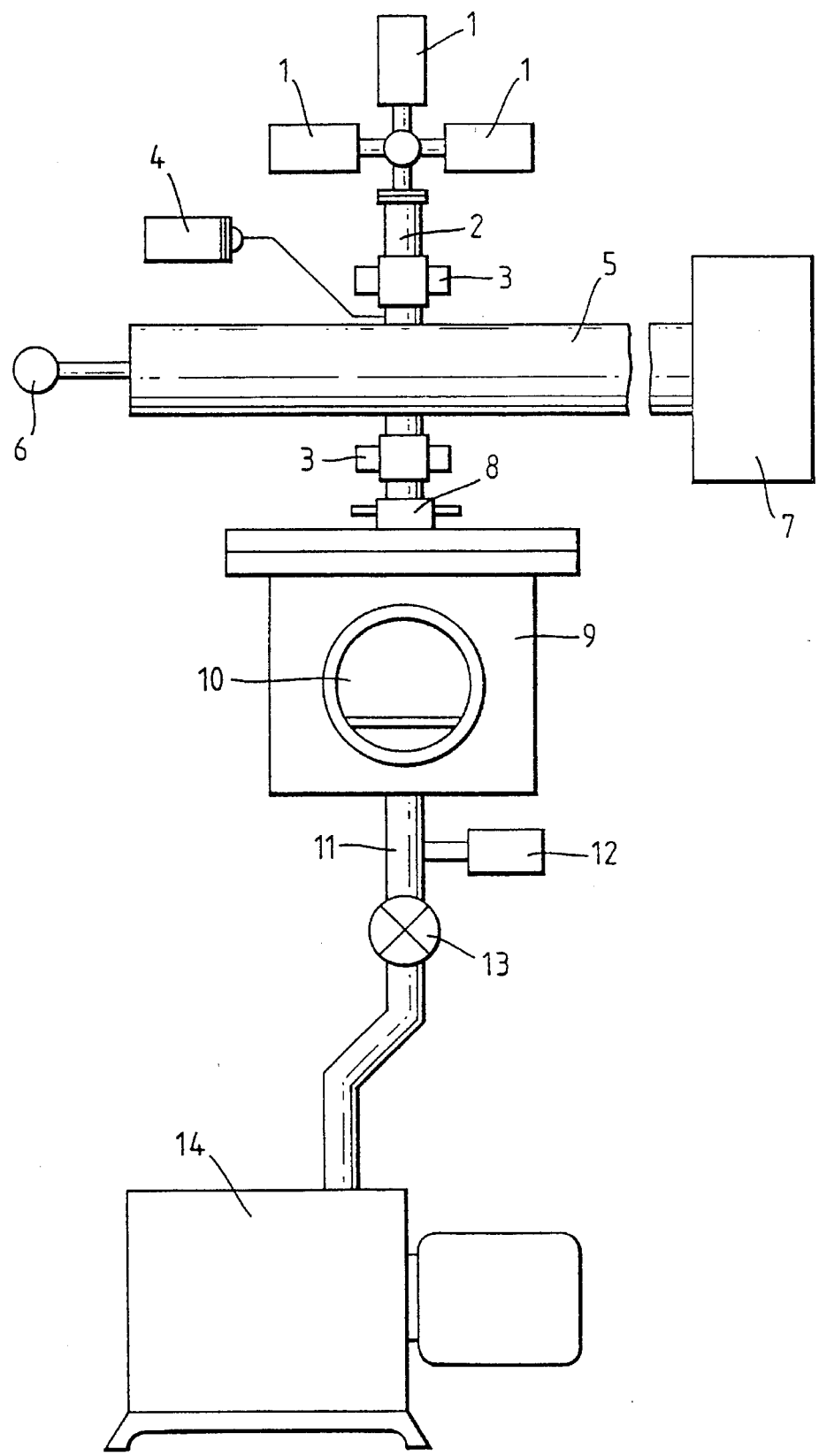

United States Patent [19]
Griffiths et al.

[11] Patent Number: 5,512,244
[45] Date of Patent: Apr. 30, 1996

[54] GAS STERILIZATION

[75] Inventors: Christopher N. Griffiths, Abingdon; David Raybone, Gloucester, both of United Kingdom

[73] Assignee: United Kingdom Atomic Energy Authority, Harwell, United Kingdom

[21] Appl. No.: 108,599

[22] PCT Filed: Feb. 20, 1992

[86] PCT No.: PCT/GB92/00304

§ 371 Date: Aug. 25, 1993

§ 102(e) Date: Aug. 25, 1993

[87] PCT Pub. No.: WO92/15336

PCT Pub. Date: Sep. 17, 1992

[30] Foreign Application Priority Data

Mar. 1, 1991 [GB] United Kingdom .................. 9104405

[51] Int. Cl.$^6$ ........................................ A61L 2/00
[52] U.S. Cl. .................................. 422/23; 422/22
[58] Field of Search ........................ 422/21–23, 906; 250/455.11

[56] References Cited

U.S. PATENT DOCUMENTS

| | | | |
|---|---|---|---|
| 3,955,921 | 5/1976 | Tensmeyer | 21/54 R |
| 4,207,286 | 6/1980 | Boncher | 422/21 |
| 4,265,747 | 5/1981 | Copa et al. | 422/23 X |
| 4,801,427 | 1/1989 | Jacob | 422/23 |
| 4,818,488 | 4/1989 | Jacob | 422/23 |
| 5,087,418 | 2/1992 | Jacob | 422/23 |
| 5,200,158 | 4/1993 | Jacob | 422/292 |
| 5,244,629 | 9/1993 | Caputo et al. | 422/22 |
| 5,413,759 | 5/1995 | Campbell et al. | 422/23 |

FOREIGN PATENT DOCUMENTS

| | | |
|---|---|---|
| 0387022 | 9/1990 | European Pat. Off. . |
| 0474137 | 3/1992 | European Pat. Off. . |
| 2654000 | 5/1991 | France . |
| 9011784 | 10/1990 | WIPO . |

Primary Examiner—Robert J. Warden
Assistant Examiner—Krisanne M. Thornton
Attorney, Agent, or Firm—William R. Hinds

[57] ABSTRACT

A method of sterilising objects including the operations of activating a gaseous medium, ensuring that the activated medium is substantially free of charged species and exposing the object to be sterilised to the activated gaseous medium for a period sufficient to ensure that the object is sterilised.

22 Claims, 2 Drawing Sheets

GAS STERILIZATION

The present invention relates to the sterilisation of medical and other equipment by means of chemically active gaseous media.

A proposed technique for sterilising medical equipment, and other objects, is to expose them to the action of a plasma. Plasmas in this context are gaseous media which contain a significant proportion of ionised species and free electrons. Examples of methods of carrying out this technique are disclosed in U.S. Pat. Nos. 3,383,163; 3,851,436; 3,948,601; 4,207,286; 4,321,232; 4,348,357; 4,643,876; Japanese Application Disclosure numbers 103460/83; 162276/83 and European Patent Application number 387022A. However, gas plasmas, although effective as sterilising agents have been found often to be too chemically aggressive, causing damage to an object being sterilised. This failing has been an inhibiting factor in the general adoption of the technique.

It is an object of the present invention to provide a method of sterilising objects by means of activated gaseous media, that is to say, gaseous media which contain significant numbers of free radicals, metastable and electronically excited species, but which do not contain significant amounts of ionised species.

According to the present invention there is provided a method of sterilising articles by exposing them to a biologically active gaseous medium, wherein there is included the operations of activating a gaseous medium to provide free radicals, and/or electronicaly and/or vibrationally excited species, ensuring that the activated gaseous medium is substantially free of charged species and exposing the article to be sterilised to the charged species free activated gaseous medium for a period sufficient to ensure that the article is sterilised.

Ionised species produced in the activation process are allowed to recombine before reaching the sterilisation chamber so that only the neutral activated gas is applied to the object to be sterilised.

The dissociation and/or electronic excitation of the gaseous medium can be achieved by means of bombardment with energetic particles, the application of DC and varying electric fields, chemically, or photo-electrically by means of electromagnetic radiation including both c.w. and high power pulsed RF and microwaves and laser radiation.

Short pulse, high power microwaves produced at a high repetition frequency are particularly effective in achieving significant dissociation whilst minimising thermal effects.

Preferably, the gaseous medium includes activating agents which increase the population of the activated species in the afterglow from the activation process. Suitable activating agents are: $SF_6$; $H_2O$; $O_2$; $H_2S$; $CO$; $C_2H_2$; $CH_4$; $Hg$; $NH_3$; $Cl_2$; $N_2O$; $NO$; $C_2H_6$ or mixtures thereof.

An activating agent can work by enhancing dissociation, enhancing or inhibiting recombination or by surface modification in a discharge chamber. It can form a component of the activated gas and can be added before or after the activating discharge.

A suitable gaseous medium for use in carrying out the present invention comprises 41%–89% by volume oxygen with the balance made up by argon, helium or nitrogen, or mixtures thereof and/or up to 9% by volume of an activating agent which can be $H_2O$; $N_2O$; $H_2$; $N_2$; $NH_3$ or NO, or mixtures thereof.

A second suitable gaseous medium for carrying out the present invention comprises 30%–99.9% nitrogen with 0.1%–9% by volume of an activating agent which can be $SF_6$; $H_2O$; $Cl_2$; NO; $O_2$; H; $CO_2$; CO; $C_2H_2$; $C_2H_6$; $CH_4$; $NH_3$; $NF_3$ or mixtures thereof, the balance being made up by argon or helium.

A third suitable gaseous medium for carrying out the invention comprises 1%–99%, oxygen with 0.1%–9% by volume of an activating agent such as $H_2O$; $N_2O$; $NH_3$, $H_2$, $N_2$ or NO, the balance being made up by argon or helium.

A fourth suitable gaseous medium is ammonia ($NH_3$) containing up to 9% by volume of an activating agent such as $N_2$; NO; $N_2O$; $H_2$; $H_2O$.

Other gas mixtures which can be used to carry out the invention are:

$N_2$ with 0.5–10% $O_2$ by volume $N_2$ with 0.5–30% $NO_2$ by volume $N_2$ with 0.5–30% NO by volume Ar with 0.5–30% $NO_2$ by volume Ar with 0.5–30% NO by volume Preferably, the excitation of the gaseous medium is carried out at a pressure in the range 0.1 to 50 mbar.

The activating agents may be added before or after the main gas is initially excited. In particular, when NO is the activating agent it is added after the initial excitation.

Figure 2:
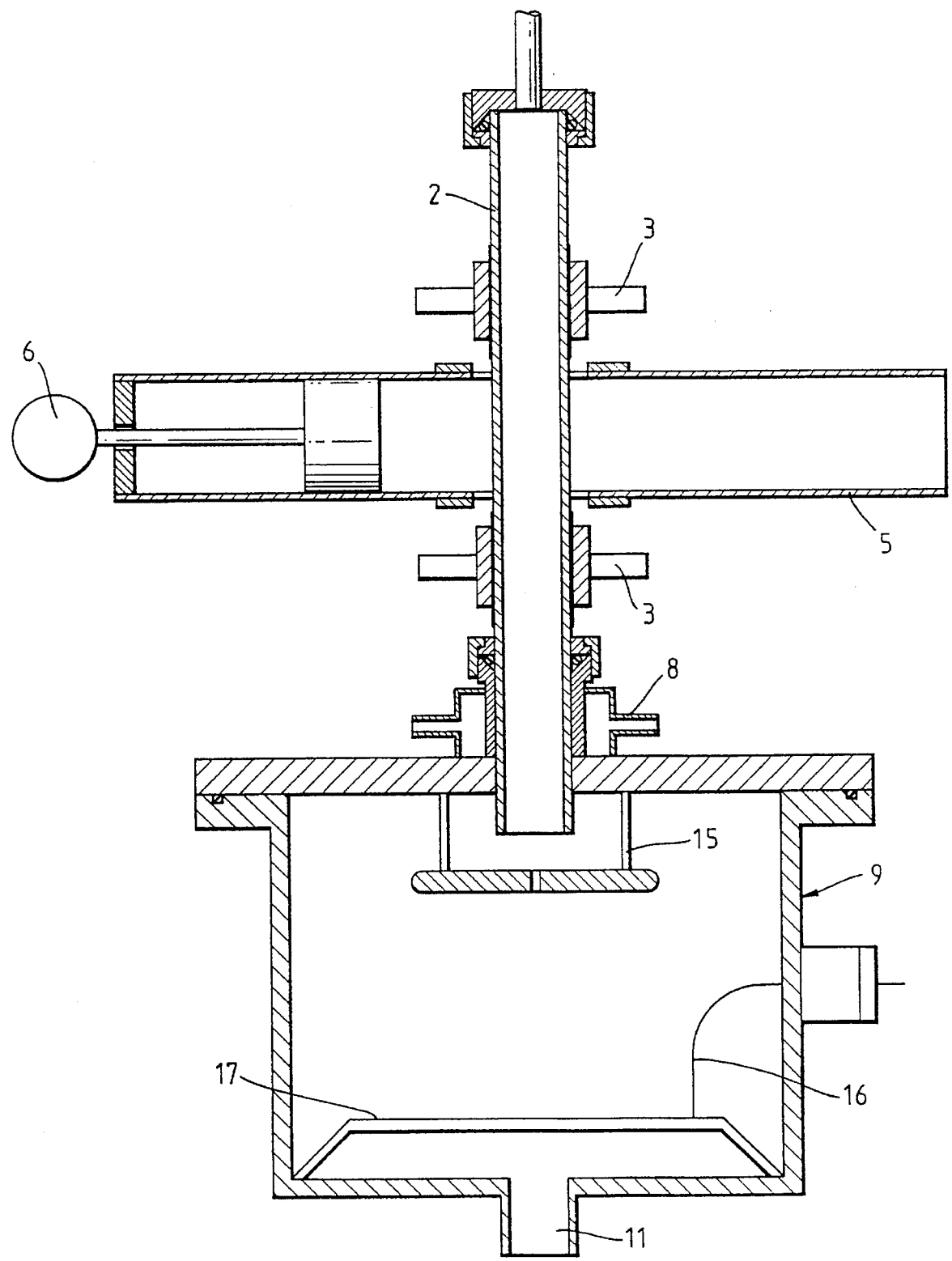

One method of sterilising bodies by means of the present invention will now be described, by way of example, with reference to the accompanying drawings, in which FIG. 1 shows, diagrammatically an apparatus in which the invention may be carried out and FIG. 2 is a cross-section of a portion of the apparatus of FIG. 1.

Referring to FIG. 1 of the drawings, gases to make up a gaseous mixture to be activated and used to sterilise equipment are supplied from reservoirs 1 in appropriate proportions, mixed and passed into a discharge tube 2 made of quartz or a ceramic material. The discharge tube 2 is surrounded by two cooling collars 3. A plasma ignition coil 4 is connected to a probe in contact with the wall of the discharge tube 2. The gaseous medium to be excited passes via the discharge tube 2 through a section of microwave waveguide 5 to one end of which there is connected a tuning short circuit 6 and to the other end of which there is connected a suitable power supply 7. Having been excited, the gaseous medium passes, via a water-cooled vacuum feedthrough 8 into a stainless steel sealed sterilisation chamber 9 in which the sterilisation process is carried out. The sterilisation operation can be observed by means of a viewing port which forms part of an access door 10 to the sterilisation chamber 9. Pressure in the sterilisation chamber 9 is maintained at a desired sub-atmospheric level by means of an exhaust connection 11, vacuum valve 13 and vacuum pump 14. The pressure within the sterilisation chamber 9 is measured by means of a vacuum gauge 12.

Referring to FIG. 2, in which those components which are common to both figures have the same reference numbers, inside the sterilisation chamber 9 there are a gas baffle 15, a thermocouple 16 and a stand 17 for objects to be sterilised.

In one method of sterilisation embodying the invention, nitrogen doped with 0.2% by volume of $SF_6/O_2$ as an activating agent was passed at a flow-rate of between 300 and 500 standard cc's per minute and a pressure between 1 and 7 mbar through an electric field in the waveguide 5 produced by microwave power between 500–800 watts.

Another method of sterilisation embodying the invention utilises a gas mixture comprising nitrogen doped with 3% by volume of oxygen as an activating agent. The gas mixture was passed through the discharge tube 2 at a flow rate of 1000 sccm at a pressure of 13 mbar. The discharge tube 2 passed through the section of waveguide 5 as before, but the microwave power was pulsed at a peak power of 250 kw at a repetition rate of 600 pulses per second and a duty cycle of 0.06%.

Any charged species produced by the discharge were removed from the gaseous medium by ensuring that the length of the manifold 2 between the waveguide 5 and the sterilisation chamber 9 was such that, in combination with flow restrictors (not shown) inserted in it, substantially all the charged species would have recombined.

Microscope slides (not shown) contaminated with Escherichia coli and Bacillus substilus were exposed to the activated nitrogen together with sulphur hexafluoride for a period of 10 minutes during which their temperature did not exceed 60° C., as shown in the following table. Subsequent bacteriological examination showed that the slides had been fully sterilised.

Other gas mixtures and operating conditions for carrying out the invention are:

| $N_2O_2$ | |
|---|---|
| $N_2$ flowrate | 1.5 sl/m |
| $O_2$ flowrate | 55 scc/m |
| microwave power | 500 W |
| Total gas pressure | 2 mbar |
| Peak temperature | 60° C. |
| $N_2/N_2O$ | |
| $N_2$ flowrate | 1.5 sl/m |
| $N_2O$ flowrate | 124 sc/m |
| microwave power | 500 W |
| Total gas pressure | 2 mbar |
| Peak temperature | 43° C. |
| $N_2/NO$ | |
| $N_2$ flowrate | 1.55 sl/m |
| NO flowrate | 23 sc/m |
| microwave power | 500 W |
| Total gas pressure | 2 mbar |
| Peak temperature | 55° C. |

In the last case, the nitric oxide is added after the initial excitation of the nitrogen.

| | | EFFECTIVE EXPERIMENTAL REGIMES | | | | | |
|---|---|---|---|---|---|---|---|
| Active Gas | Activation Agent | Flow Rate of Active Gas (Standard c.c per minute) | Flow Rate of Activation Agent (Standard c.c per minute) | Microwave Power | Exposure Time (Mins) | Peak Temp (0° C.) | Pressure (Millibar) |
| 1. $N_2$ | | 300 sscm | | 500 W | 10 min | 35° C. | 2 mbar |
| 2. $N_2$ | $SF_6$ | 300 sscm | 2 sscm | 500 W | 10 min | 35° C. | 2 mbar |
| 3. $N_2$ | $SF_6$ | 300 sscm | 0.5 sscm | 500 W | 10 min | 36° C. | 6 mbar |
| 4. $N_2$ | $O_2$ | 1000 sscm | 4 sscm | Pulsed 250 Kw peak | 30 min | 60° C. | 13 mbar |

We claim:

1. A method of sterilising articles by exposing them to a biologically active gaseous medium, comprising the operations of activating a gaseous medium to provide free radicals, and/or electronically and/or vibrationally excited species, ensuring that the activated gaseous medium is substantially free of electrically charged species, and exposing the article to be sterilised to only the charged-species-free activated gaseous medium for a period sufficient to ensure that the article is sterilised.

2. A method according to claim 1 wherein the activating of the gaseous medium comprises the dissociation and/or electronic excitation of the gaseous species achieved by means of bombardment of the gaseous species with energetic particles, the application of DC and varying electric fields, chemically, or by means of electromagnetic radiation.

3. A method according to claim 2 where the dissociation and/or excitation is achieved by means of mocrowave or RF radiation.

4. A method according to claim 2 wherein the electromagnetic radiation is in the form of a laser beam.

5. A method according to claim 1 wherein the gaseous medium includes activating agents adapted to enhance the production of free radicals and maximise the effective lifetime of the activated species.

6. A method according to claim 5 wherein the activating agent is selected from the group consisting of $SF_6$; $H_2O$; $O_2$; $H_2S$; CO; $C_2H_2$; Hg; NO; $Cl_2$; $N_2O$; $C_2H_6$ or mixtures thereof.

7. A method according to claim 1 wherein the gaseous medium comprises 41%–89% by volume oxygen with the balance made up by gas selected from the group consisting of argon, helium or nitrogen or mixtures thereof.

8. A method according to claim 7 wherein the gaseous medium includes up to 9% by volume of an activating agent selected from the group consisting of $H_2O$; $N_2O$; $H_2$; NO or mixtures thereof.

9. A method according to claim 1 wherein the gaseous medium comprises oxygen including up to 9% by volume of an activating agent selected from the group consisting of $H_2O$; $N_2O$; $H_2$; $N_2$; NO or mixtures thereof.

10. A method according to claim 1 wherein the gaseous medium comprises 30%–99.9% by volume nitrogen with 0.1%–9% by volume of an activating agent selected from the group consisting of $SF_6$; $H_2O$; $Cl_2$; NO; $O_2$; $H_2$; $CO_2$; CO; $C_2H_6$; $CH_4$; $NF_3$ or mixtures thereof.

11. A method according to claim 1 wherein the gaseous medium comprises 1%–99% by volume oxygen with 0.1%–9% by volume of an activating agent selected from the group consisting of $H_2O$; $N_2$O or NO and the balance made up of argon or helium.

12. A method according to claim 1 wherein the gaseous medium comprises ammonia ($NH_3$) containing up to 9% by volume of an activating agent selected from the group consisting of $N_2$; NO; $H_2$; $H_2O$.

13. A method according to claim 6 wherein the gaseous medium comprises nitrogen with 0.5–10% $O_2$, by volume.

14. A method according to claim 6 wherein the gaseous medium comprises nitrogen with 0.5–30% $N_2O$, by volume.

15. A method according to claim 6 wherein the gaseous mixture comprises nitrogen with 0.5–30% NO, by volume.

16. A method according to claim 6 wherein the gaseous mixture comprises nitrogen with 0.5–30% $N_2O$ or NO, by volume.

17. A method according to claim 1 wherein the excitation of the gaseous medium is carried out at a pressure in the range of 0.1 to 50 m bar.

18. A method according to claim 1 wherein excitation of the gaseous medium is achieved by passing it through an electric field produced by microwave power of at least 500 watts.

19. A method according to claim 1 wherein the gaseous medium comprises nitrogen with 0.2% by volume of $SF_6$.

20. A method according to claim 18 wherein the gaseous medium is excited initially by passing it at a flow rate of 500 standard cubic centimeters per minute and a pressure of between 1 and 7 m bar through an electric field produced by microwave power in the region of 500–800 watts.

21. A method according to claim 1 wherein the gaseous medium is cooled after activation.

22. A method as claimed in claim 1 wherein any charged species produced when activating the gaseous medium are removed by causing them to recombine before exposing the article to the activated gaseous medium.

* * * * *